United States Patent
Rosiwal et al.

(10) Patent No.: US 11,793,733 B2
(45) Date of Patent: Oct. 24, 2023

(54) IMPLANT OR MEDICAL TOOL MADE OF A METAL

(71) Applicant: FRIEDRICH-ALEXANDER-UNIVERSITAET ERLANGEN-NUERNBERG, Erlangen (DE)

(72) Inventors: Stefan Rosiwal, Bamberg (DE); Marie Schumann, Freiburg (DE)

(73) Assignee: FRIEDRICH-ALEXANDER-UNIVERSITAET ERLANGEN-NURNBERG, Erlangen (DE)

( * ) Notice: Subject to any disclaimer, the term of this patent is extended or adjusted under 35 U.S.C. 154(b) by 564 days.

(21) Appl. No.: 16/760,851

(22) PCT Filed: Oct. 31, 2018

(86) PCT No.: PCT/EP2018/079896
§ 371 (c)(1),
(2) Date: Apr. 30, 2020

(87) PCT Pub. No.: WO2019/086551
PCT Pub. Date: May 9, 2019

(65) Prior Publication Data
US 2021/0212905 A1 Jul. 15, 2021

(30) Foreign Application Priority Data
Nov. 2, 2017 (DE) ............. 10 2017 125 635.0

(51) Int. Cl.
*A61K 6/831* (2020.01)
*A61K 6/838* (2020.01)
(Continued)

(52) U.S. Cl.
CPC ............. *A61K 6/831* (2020.01); *A61K 6/838* (2020.01); *A61K 6/84* (2020.01); *A61N 1/05* (2013.01);
(Continued)

(58) Field of Classification Search
CPC ............. A61N 1/05; A61N 1/20; A61N 1/32
See application file for complete search history.

(56) References Cited

U.S. PATENT DOCUMENTS 5,900,127 A * 5/1999 Iida .................. C02F 1/46109
204/290.14
2007/0032877 A1 * 2/2007 Whiteside ............ A61L 27/303
623/22.15
(Continued)

FOREIGN PATENT DOCUMENTS

DE 299 16 126 U1 1/2000
EP 3 323 380 A1 5/2018
(Continued)

OTHER PUBLICATIONS

Alcaide et al., "Boron-Doped Nanocrystalline Diamond Electrodes for Neural Interfaces: In vivo Biocompatibility Evaluation," Frontiers in Neuroscience, vol. 10, Article 87, 9 pages (Mar. 8, 2016).
(Continued)

*Primary Examiner* — Mallika D Fairchild
(74) *Attorney, Agent, or Firm* — Prismatic Law Group, PLLC; Ronald J. Kamis

(57) ABSTRACT

The invention relates to an implant or medical tool made of a metal or having a surface made of a metal for use in a therapeutic treatment, wherein the implant or the tool has, on its/the surface, a coating with polycrystalline doped electrically conductive diamond, wherein the therapeutic therapy is a treatment of a microbial infection of a human or animal body,
(Continued)

Figure 1:
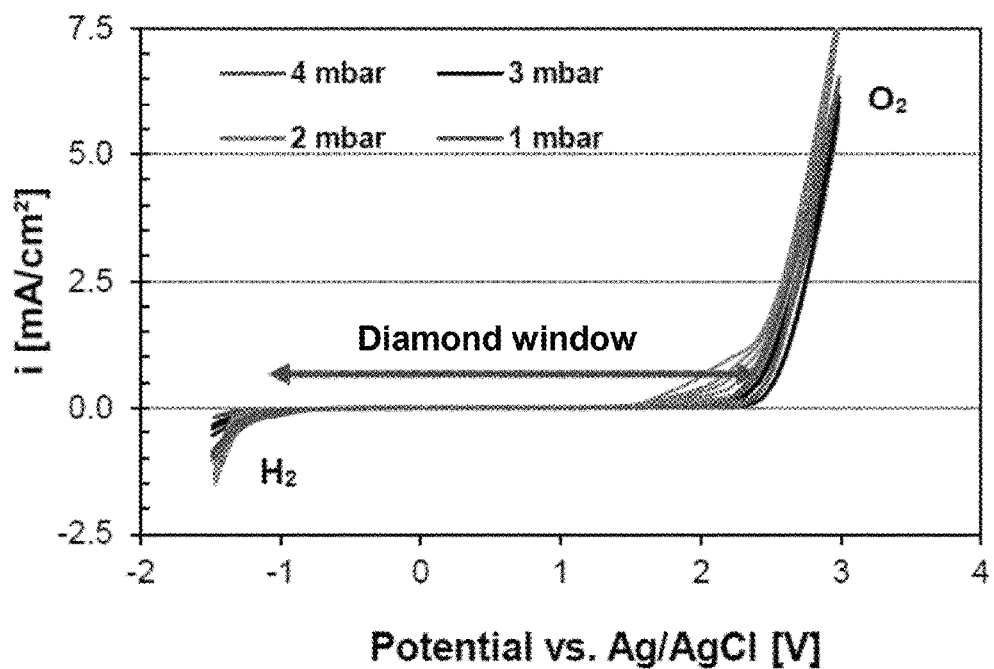

wherein the implant or the tool is connected as anode (12) in an electrochemical system in the body, wherein the electrochemical system comprises, in addition to the anode (12), a cathode (16), a power source connected in an electrically conductive manner to the anode and to the cathode, and an electrolyte comprising or consisting of a body fluid, or consists of the anode (12), a cathode (16), a power source connected in an electrically conductive manner to the anode and to the cathode, and an electrolyte comprising or consisting of a body fluid, or wherein the implant or the tool is disposed within an electrical field, by means of which a negative charge is induced at a first site and a positive charge at a second site by induction on the implant or tool, by means of which the first site becomes the anode (12) in an electrochemical system and the second site becomes the cathode (16) in the electrochemical system, wherein the electrochemical system comprises, in addition to the implant or the tool, an electrolyte comprising or consisting of a body fluid or consists of the implant or the tool and an electrolyte comprising or consisting of a body fluid.

18 Claims, 5 Drawing Sheets

(51) Int. Cl.
  A61K 6/84 (2020.01)
  A61N 1/32 (2006.01)
  A61N 1/20 (2006.01)
  A61N 1/05 (2006.01)
  A61C 5/42 (2017.01)
  A61L 31/08 (2006.01)

(52) U.S. Cl.
  CPC .............. A61N 1/20 (2013.01); A61N 1/32 (2013.01); *A61C 5/42* (2017.02); *A61L 31/084* (2013.01); *A61L 31/086* (2013.01); *A61L 31/088* (2013.01); *A61L 2420/02* (2013.01)

(56) References Cited

U.S. PATENT DOCUMENTS

| | | | | |
|---|---|---|---|---|
| 2015/0080906 A1* | 3/2015 | Fjorback | .............. | A61N 1/0558 607/116 |
| 2015/0282907 A1* | 10/2015 | Zipprich | .............. | A61C 8/0093 433/32 |
| 2016/0000947 A1* | 1/2016 | Brodbeck | .......... | A61C 17/0202 433/32 |

FOREIGN PATENT DOCUMENTS

| | | |
|---|---|---|
| JP | 2017-159002 A | 9/2017 |
| WO | 02/45589 A2 | 6/2002 |
| WO | 2014/015444 A1 | 1/2014 |
| WO | 2016/017694 A1 | 2/2016 |

OTHER PUBLICATIONS

Booth et al., "Synthesis and Characterization of Multilayered Diamond Coatings for Biomedical Implants," Materials, vol. 4, pp. 857-868 (May 9, 2011).

Database WPI, AN 2016-11166H, vol. 2016, No. 15, Thomson Scientific, London, GB, 2 pages (2016).

Database WPI, AN 2017-64230T, vol. 2017, No. 63, Thomson Scientific, London, GB, 1 page (2017).

Garrett et al., "In vivo biocompatibility of boron doped and nitrogen included conductive-diamond for use in medical implants," J. Biomed Mater Res Part B, vol. 104B, pp. 19-26 (2016, published online Jan. 21, 2015).

Ghemaout, "Microorganisms' Electrochemical Disinfection Phenomena," EC Microbiology, vol. 9, No. 4, pp. 160-169 (Jul. 13, 2017).

Hubler et al., "Understanding Chlorite and Chlorate Formation Associated with Hypochlorite Generation at Boron Doped Diamond Film Anodes," J. Electrochem. Soc., vol. 161, No. 12, pp. E182-E189 (Sep. 17, 2014).

Kraft, "Doped Diamond: A Compact Review on a New, Versatile Electrode Material," Int. J. Electrochem. Sci., vol. 2, pp. 355-385 (May 1, 2007).

Kromka et al., "Semiconducting to metallic-like boron doping of nanocrystalline diamond films and its effect on osteoblastic cells," Diamond & Related Materials, vol. 19, pp. 190-195 (2010, published online Oct. 13, 2009).

Mohn et al., "Electrochemical Disinfection of Dental Implants—a Proof of Concept," PLoS One, vol. 6, Issue 1, e16157, 6 pages (Jan. 14, 2011).

Neuerer, "Beeinflussung der Titankarbid-Schichtdicke bei der HFCVD—Diamantbeschichtung von Titan durch Oberflächenvorbehandlungen und Variation der Beschichtungsparameter," Der Technischen Fakultät der Universität Erlangen-Nürnberg zur Erlangung des Grades (2013).

Ochiai et al., "Application of Boron-Doped Diamond Microelectrodes for Dental Treatment with Pinpoint Ozone-Water Production," ChemPhysChem, vol. 14, pp. 2094-2096 (2012).

Sahrmann et al., "Effect of Low Direct Current on Anaerobic Multispecies Biofilm Adhering to a Titanium Implant Surface," Clinical Implant Denistry and Related Research, vol. 16, No. 4, pp. 552-556 (Nov. 21, 2012).

* cited by examiner

IMPLANT OR MEDICAL TOOL MADE OF A METAL

CROSS-REFERENCE TO RELATED APPLICATIONS

This application is a 371 National Phase of International Patent Application No. PCT/EP2018/079896 filed on Oct. 31, 2018, which claims priority to DE 10 2017 125 635.0 filed on Nov. 2, 2017, the content of each of which applications is incorporated herein by reference.

The invention relates to an implant made of a metal. This may, for example, be a dental implant or a jaw implant or what is called an endoprosthesis, especially an endoprosthesis for replacement of a bone or a joint. It may alternatively also be an article introduced into the body only for a comparatively short period of time. The invention further relates to a medical tool, especially a surgical tool.

It is known that bacteria that have been introduced from outside or endogenously displaced can adhere to implant surfaces. This can lead to an inflammation reaction that damages the surrounding tissue. Owing to a loss of function resulting from septic loosening or the effect of the implant as a source of infection, this can necessitate the removal of the implant by operation.

For avoidance of such infections, gentamicin coatings of endoprostheses are known. The antibiotic gentamicin is released locally here from a polymer carrier material. The polymer carrier material is subsequently degraded in the body. However, the antibacterial effect lasts only for a relatively short time. In addition, the antibiotic is problematic owing to resistance formation.

It is additionally known that endoprostheses can be provided with antibacterial copper and silver coatings. However, metal ions released by these coatings can also have a harmful effect on the surrounding tissue.

The thesis by Neuerer, K. "Beeinflussung der Titankarbid-Schichtdicke bei der HFCVD-Diamantbeschichtung von Titan lurch Oberflächenvorbehandlungen and Variation der Beschichtungsparameter" [Influencing the Titanium Carbide Layer Thickness in the HFCVD Diamond Coating of Titanium by Surface Pretreatments and Variation of the Coating Parameters] from the technical faculty of the University of Erlangen-Nuremberg, 2013, discloses coating titanium with boron-doped diamond by means of hot filament chemical vapor deposition. The coating becomes electrically conductive by virtue of the boron doping, such that the titanium coated in this way can be used as electrode. In addition, the thesis also discloses that the coating of titanium electrodes with boron-doped diamond forms a titanium carbide interlayer between the diamond layer and the titanium substrate.

The thesis also discloses the use of boron-doped diamond electrodes for electrochemical water purification, especially for disinfection and treatment of drinking water. The great advantage of diamond electrodes here is the generation of oxidizing agents at the anode owing to the high overvoltage for the electrolysis of water. Hydroxyl radicals are formed directly from the water at the electrode, and these, together with secondary oxidizing agents, for example active chlorine and ozone, achieve a cleaning effect. With electrochemical cells, it was thus possible to effectively inactivate legionella, *Escherichia coli* bacteria and other microbes.

Kraft, A., "Doped Diamond: A Compact Review on a New, Versatile Electrode Material", International Journal of Electrochemical Science, 2 (2007), pages 355 to 385, discloses the use of doped diamond electrodes for water and wastewater treatment.

Djamel Ghernaout, "Microorganisms' Electrochemical Disinfection Phenomena", EC Microbiology 9.4 (2017), pages 160 to 169, discloses various mechanisms for killing of microorganisms for disinfection and various electrode materials suitable for the purpose, for example boron-doped diamond.

Garrett, D. et al., "In vivo biocompatibility of boron doped and nitrogen included conductive-diamond for use in medical implants", J Biomed Mater Res B Appl Biomater, 2016 January, 104(1), pages 19 to 26, discloses a study of the biocompatibility of implants made of electrically conductive boron-doped diamond in guinea pigs. The authors conclude from the results of the study that boron-doped diamond is a safe material for implanting.

Kromka, A. et al., "Semiconducting to metallic-like boron doping of nanocrystalline diamond films and its effect on osteoblastic cells", Diamond & Related Materials 19 (2010), pages 190 to 195, describes the influence of the level of boron doping of nanocrystalline diamond films on silicon carriers on the adhesion, proliferation and differentiation of osteoblastic cells. All the substrates examined showed good biocompatibility and stimulated the adhesion and growth of the cells examined.

Booth, L. et al., "Synthesis and Characterization of Multilayered Diamond Coatings for Biomedical Implants", Materials (Basel), 2011 May; 4(5), pages 857 to 868, discloses a multilayer diamond coating with alternating nanocrystalline and microcrystalline diamond layers on surfaces of Ti-6Al-4V.

Alcaide, M. et al., "Boron-Doped Nanocrystalline Diamond Electrodes for Neural Interfaces: In vivo Biocompatibility Evaluation", Frontiers in Neuroscience, Vol. 10, Article 87, March 2016, discloses implantable boron-doped nanocrystalline diamond electrodes for neural stimulation.

It is an object of the present invention to specify a metal implant having a surface coating with boron-doped diamond for use in an alternative therapeutic treatment.

The object is achieved by the features of patent claim 1. Advantageous configurations are apparent from the features of patent claims 2 to 12.

The invention provides an implant or medical tool made of a metal or having a surface made of a metal for use in a therapeutic treatment, wherein the implant or the tool, on its/the surface, has a coating with polycrystalline doped electrically conductive diamond. The therapeutic treatment here is a therapy of a microbial infection of a human or animal body, especially associated with an inflammation reaction. The therapy here may be a therapy that prevents the microbial infection or a therapy that heals the microbial infection. The medical tool may be a surgical tool, for example a scalpel or a rotating surgical instrument, especially a rotating dental instrument, especially a dental drill.

The implant or tool here is connected as anode in an electrochemical system in the body. The electrochemical system here comprises, in addition to the anode, a cathode, a power source connected in an electrically conductive manner to the anode and to the cathode, and an electrolyte comprising or consisting of a body fluid, or consists of the anode, a cathode, a power source connected in an electrically conductive manner to the anode and to the cathode, and an electrolyte comprising or consisting of a body fluid. The cathode here may consist of a standard electrode material. The electrode material may, for example, be platinum, steel, especially stainless steel, carbon, especially in the form of graphene, or, especially in the case of a cathode disposed in the human or animal body, titanium or boron-doped diamond-coated titanium or steel. The electrically conductive connection of the anode and of the cathode to the power source may be via an electrically conductive wire or metal pin. The power source is generally a DC power source that may be disposed in the human or animal body, for example in the form of a battery or accumulator. It may alternatively be disposed outside the human or animal body and may, for example, be a battery or accumulator or a transformer or mains power supply that provides a defined DC voltage.

Alternatively, it is possible that the implant or the tool is disposed within an electrical field, by means of which a negative charge is induced at a first site and a positive charge at a second site by induction on the implant or tool, by means of which the first site becomes the anode in an electrochemical system and the second site becomes the cathode in the electrochemical system, wherein the electrochemical system comprises, in addition to the implant or the tool, an electrolyte comprising or consisting of a body fluid or consists of the implant or the tool and an electrolyte comprising or consisting of a body fluid. Such an arrangement is referred to as a bipolar arrangement.

The electrical field may be built up here between a further anode and a further cathode within the electrochemical system. The electrochemical system in this case additionally comprises, in addition to the further anode and the further cathode, a power source connected in an electrically conductive manner to the further anode and the further cathode, or additionally consists of the further anode and the further cathode and a power source connected in an electrically conductive manner to the further anode and the further cathode.

The electrolyte in the electrochemical system may comprise an electrically conductive auxiliary fluid or consist of the body fluid and the electrically conductive auxiliary fluid. The electrically conductive auxiliary fluid here is a liquid that establishes electrical contact of the further anode and of the further cathode with the body fluid. The auxiliary fluid therefore contains ions and may, for example, be a saline solution. The auxiliary fluid may be in the form of a gel. If the further anode and the further cathode are disposed on the skin of the human or animal body, the auxiliary fluid may be disposed between the skin and the further anode and between the skin and the further cathode in order to establish electrical contact of the further anode and the further cathode with the body fluid.

The electrical field may also be built up between at least two plates, especially disposed outside the electrochemical system, of a capacitor or by at least one electrical coil, especially disposed outside the electrochemical system. The two plates of the capacitor here form a pair of capacitor plates.

It is additionally possible that the alignment of the electrical field is altered during the therapeutic treatment. This can be effected, for example, by rotating the at least two plates of the capacitor around the body or part of the body in which the implant is present. As a result, there is then also rotation of the electrical field and the positions of the first and second sites on the implant or tool. In the therapeutic treatment, it is also possible to reverse the polarity of the plates of the capacitor, so as to alternate the positions of the first and second sites on the implant or tool. It is also possible to provide more than one pair of capacitor plates and to build up the electrical field sequentially or alternately between one of the pairs of capacitor plates at a time. In this way too, it is possible to alter the alignment of the electrical field during the therapeutic treatment and especially to rotate the electrical field. The animal body may especially be an animal body of a mammal. The body fluid may also be a body fluid present in a body tissue. The body fluid may, for example, also be blood, lymph or sweat, or two or more different liquids in the human or animal body, or a mixture of at least two of these liquids. The body tissue may be a hard tissue or a soft tissue.

The electrical conductivity of the polycrystalline diamond is achieved by the doping. For this purpose, the diamond may be doped with boron or phosphorus.

The inventors of the present invention have recognized that an implant or medical tool made of a metal or having a surface made of metal with a surface coating of polycrystalline doped electrically conductive diamond has very good usability for therapy of a microbial infection of a human or animal body, especially owing to microbial colonization of the implant. The inventors have found that such an implant or tool is suitable both for inactivation of individual and adherent cells and for inactivation of microorganisms present in complex biofilms. For this purpose, a voltage of good suitability is in the range from 3 V to 15 V, especially 4 V to 6 V. The inactivation mentioned may alternatively be achieved even with a voltage of at least 2 V. After the inactivation of microorganisms present in the biofilms, the biofilms and the microorganisms are typically degraded by endogenous mechanisms.

Boron-doped diamond (BDD) has a potential window of 3.5 V. With BDD connected as anode in an electrochemical system, it is possible within this potential window to directly produce OH radicals at the anode because there is no electrolytic splitting of oxygen from water at the anode within this potential window. The following reaction proceeds here at the anode:

Within this voltage range, hydrogen forms at the cathode according to the following reaction:

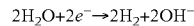

In the electrochemical window it is possible to form further oxidizing products in addition to OH radicals, for example $O_3$, $O_2$, $Cl_2$, $H_2O_2$, $C_2O_6^{2-}$, $S_2O_8^{2-}$, $P_2O_8^{4-}$ or $ClO^{2-}$. As soon as the potential applied is greater or smaller than the potential window, water is broken down. FIG. 1 illustrates this relationship.

The current density-potential curve of FIG. 1 was measured on boron-doped diamond layers having layer thicknesses in the range from 3 to 8 µm on p-doped Si wafers versus an Ag/Aga electrode. The diamond layers were produced at various pressures. The electrolyte used here was acetic acid with $Na_2SO_4$ as conductive salt. Within the diamond window, owing to the overvoltage of diamond, oxidizing products are formed. Outside that, water is additionally split. The rise at about 2.8 V shows the commencement of the anodic evolution of oxygen by the breakdown of water. At about −1.3 V, the curve drops owing to cathodic hydrogen production. The curve is not generally applicable. The size of the diamond window may vary therefrom in the case of a current density-potential measurement with a different cathode and/or different anode. For instance, a cathode with a diamond coating having a varying grain size within the diamond may result in a different current density-potential curve than that shown in FIG. 1. For example, an anode having a diamond layer consisting predominantly of diamond with a grain size in the nanosize range results in a smaller potential window than the potential window apparent from FIG. 1. The diamond layer of the anode used in the experiment shown in FIG. 1 had a grain size in the range from 2 to 3 µm.

The inventors have found that microorganisms, especially bacteria that reside on the surface of boron-doped diamond, can be efficiently damaged electrochemically such that they die off when the implant made of metal with the diamond surface is connected as anode. It is already sufficient here to apply a minimal voltage, for example of 1.23 V, to form products having antimicrobial action at the anode. The antimicrobial action of the implant of the invention may be based here firstly on the formation of hydroxyl radicals (OH·) and secondly on the formation of oxidizing agents or reaction products of the hydroxyl radicals. Oxidizing agents, i.e. oxidizing products, may already form at lower potentials than the potential required for the formation of hydroxyl radicals. Table 1 below shows which oxidizing products can form at what potential within the diamond window.

TABLE 1

| Oxidizing products | BDD electrode potential [V] |
|---|---|
| $O_2$ | 1.23 |
| $Cl_2$ | 1.36 |
| $ClO^{2-}$ | 1.57 |
| $H_2O_2$ | 1.77 |
| $C_2O_6^{2-}$ | 1.80 |
| $S_2O_8^{2-}$ | 2.01 |
| $P_2O_8^{4-}$ | 2.07 |
| $O_3$ | 2.07 |
| OH• | 2.80 |

The therapeutic treatment in which the implant is connected as anode in the electrochemical system, i.e. in which an electrical voltage is applied to the electrochemical system by means of the power source, is typically effected only for a few minutes at a time. However, it can be repeated several times. The voltage applied for the purpose may also be outside the diamond window. It is also possible here to form gaseous products, for example $O_2$, $O_3$, or $CO_2$ or CO from the carbon in the human or animal cells surrounding the implant. In the case of implants within a closed region of the body, the voltage should be chosen such that the amount of gaseous products formed at the anode is sufficiently low that these can dissolve directly in the body fluid after they have formed. The anode is not recognizably attacked within the relatively short treatment time overall and at the low voltage.

Experiments conducted in a cell culture model have shown that, in a treatment effected for just a few minutes at a time, hence corresponding to a possible actual therapeutic treatment, there is at least no significant damage, if any, to healthy cells that surround the implant in the human or animal body, and hence also no significant damage to healthy tissue surrounding the implant in the human or animal body. By contrast, damage to inflammatory cells or endogenous cells previously damaged by inflammation is possible and indeed desirable in the therapy of a microbial infection. The minor degree of damage at worst compared to the healthy cells that surround the implant in the human or animal body distinguishes the implant of the invention from a silver-coated implant that releases silver ions or another implant that releases toxic metal ions that can have a toxic effect on such cells. Since the toxic ions are released permanently by such an implant, but the implant of the invention has antimicrobial action only in the event of application of a voltage, it is also possible for any hitherto unknown tissue-damaging effect to occur only during the short time in which a voltage is applied. The antimicrobial action of the implant or tool of the invention can be switched on or off at any time.

The implant of the invention enables the control of any implant-associated infection and the avoidance of any complication caused by such an infection. The complication may, for example, be peri-implant mucositis in the case of a dental implant, a loss of function of the implant as a result of septic loosening of the implant, an effect of the implant as an infection source, or destruction of tissue surrounding the implant as a result of an inflammation reaction.

The microbial infection may be a bacterial infection, but also a fungal infection.

The metal may be titanium or a titanium-containing alloy. Titanium has particularly good suitability as material for an implant by virtue of its hardness and the ability of tissue to heal well around it as an implant, especially in the case of replacement of joints or in the case of use in a jawbone. The coating of titanium with doped diamond is possible without difficulty by means of known techniques.

The alloy may be Ti-6Al-4V, Ti-6Al-7Nb or another alloy containing, in addition to titanium, aluminum and/or niobium and/or iron and/or molybdenum.

The coating may be a coating produced on the surface of the implant or the tool in a gas phase containing a boron containing compound by hot filament chemical vapor deposition (HFCVD) or by microwave plasma-assisted chemical vapor deposition (MPCVD) or by another kind of chemical vapor deposition (CVD). The boron containing compound may, for example, especially be boron trioxide, diborane, triethylborane or trimethyl borate. The coating of titanium substrates with diamond for use as electrode material is known in the art. In sustained industrial operation, these electrodes do not have sufficient stability over an operating period of about 100 hours, but this is not a factor in the end use envisaged in accordance with the invention, in which the implant is connected as anode only for a limited and relatively short time overall of typically not more than 10 hours.

When the metal is titanium or the titanium-containing alloy, there may be an interlayer of titanium carbide (TiC) between the titanium or the alloy and the coating. Titanium carbide forms spontaneously on the titanium surface or the titanium-containing surface during the coating process by reaction of titanium with the carbon-containing atmosphere. In the case of coating by means of chemical vapor deposition, diamond growth and titanium carbide growth compete for the carbon present in the gas phase. However, as soon as a continuous diamond layer has formed, the growth of the titanium carbide layer has ended. The titanium carbide layer imparts good adhesion of the diamond layer on the titanium. However, it also significantly affects the lifetime of the diamond electrode formed. A high temperature of the titanium substrate in the coating process promotes the formation of a thick and brittle titanium carbide layer, the high thermal stress of which can result in flaking-off of the diamond layer and hence a reduction in the stability of the electrodes.

In order to reduce the thickness of the titanium carbide layer and hence improve the electrochemical stability of the diamond electrodes, it is possible to choose a comparatively low substrate temperature and a comparatively high methane flow in the coating operation. A further means of reducing the thickness of the titanium carbide layer is that of oxidation of the titanium surface prior to the coating operation.

The implant of the invention has been found to have particularly good antimicrobial action when the interlayer does not exceed a layer thickness of 3 μm, especially 2.5 μm, especially 2 μm. A layer thickness of the interlayer of at least 100 nm has also been found to be favorable for good stability of the surface coating. The diamond layer may have a layer thickness of 100 nm to 10 μm, especially 2 μm to 3 μm, especially 2 μm to 2.8 μm.

The implant may be a dental implant or jaw implant accessible from outside the body without surgical intervention and may be electrically contacted for the therapy from outside the body. For this purpose, the cathode may be positioned in the oral cavity or on the skin such that current flow is possible. The power source here is typically outside the body.

It is also possible that the implant has been implanted within the body and an electrical conductor, especially an electrically conductive wire, is routed from the implant to an outside of the body and is electrically contacted on the outside for the therapy. The implant may also be a temporary implant. A temporary implant may, for example, be an operation instrument during an operative intervention or a special wire placed within the body for a short period of time, for instance in the event of a heart catheter examination, or an electrode placed within the body for a short period of time. The medical or surgical tool may be a scalpel, for example.

In another configuration, the electrical conductor is routed from the implant to a contact site beneath the skin which contact site is electrically contacted for the therapy from the outside through a puncture. In both cases, the cathode may be introduced into the body through a puncture or positioned on the skin.

In a further alternative configuration, the electrical conductor is routed from the implant via an electrical rectifier to a coil, especially disposed not more than 3 cm beneath the skin, and connected thereto in an electrically conductive manner. The coil in this case is also connected to the cathode in an electrically conductive manner via the electrical rectifier. The cathode here is likewise disposed within the body. For the therapy, a flow of current is induced in the coil by induction from outside the body, by means of which the cathode and the anode are energized.

This enables a therapy without a puncture and without a further surgical intervention into the body apart from the surgical intervention required to insert the implant. The coil here forms the power source or at least part of the power source which is supplied with energy by means of induction from an external power source.

Figure 2:
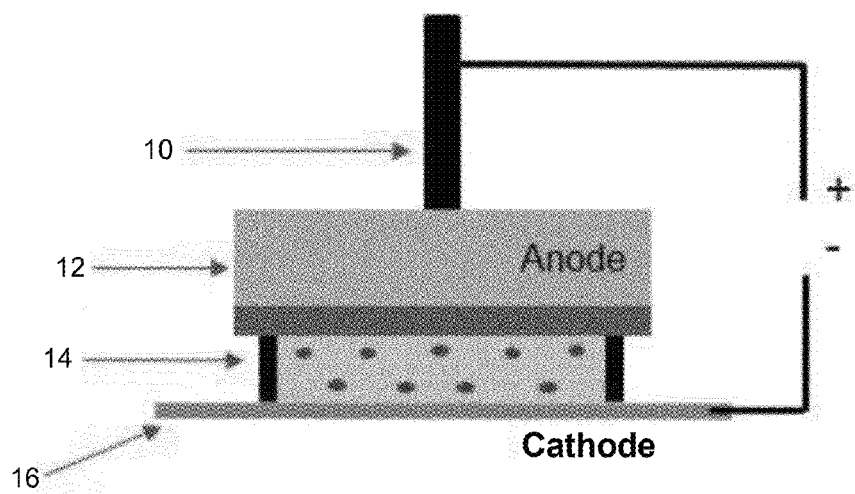
Figure 3:
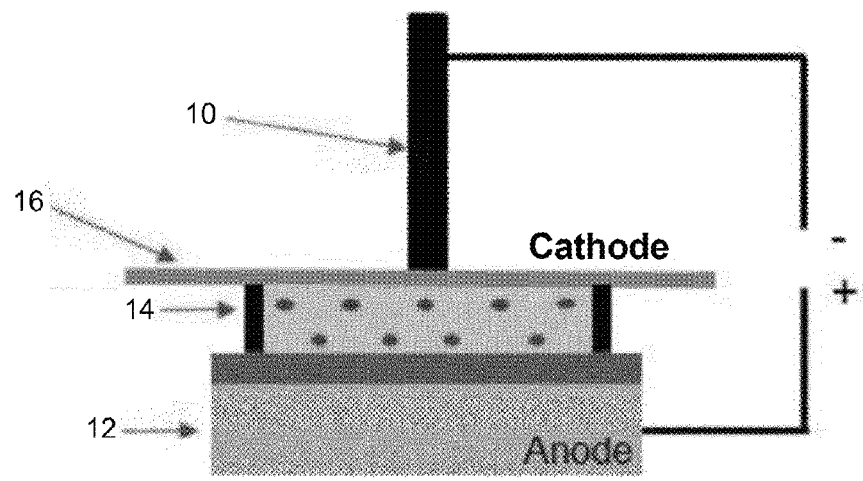
Figure 4:
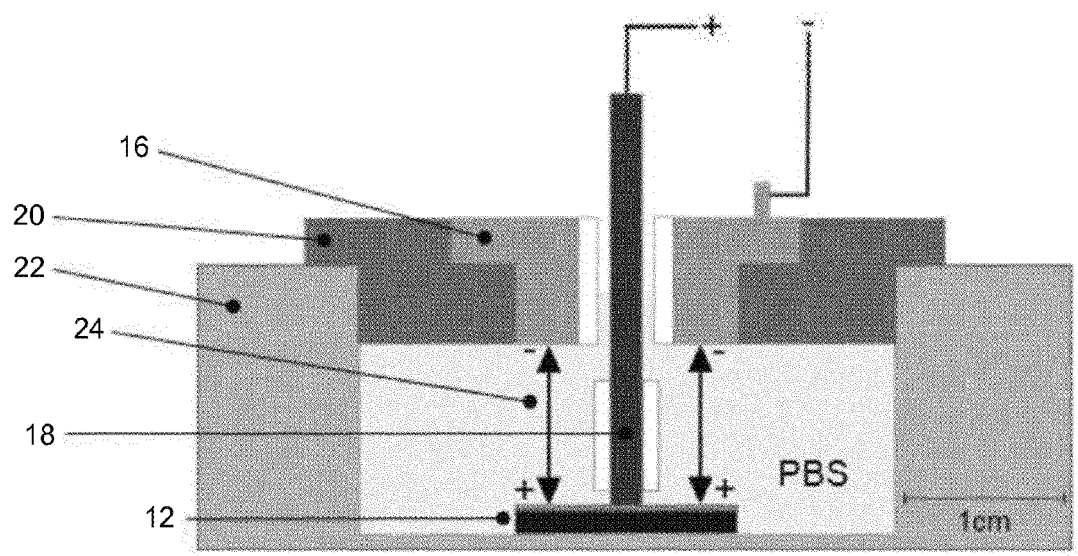

The invention is elucidated in detail hereinafter with reference to working examples. The figures show:

FIG. 1 a current density-potential curve on boron-doped diamond layers,

FIG. 2 an experimental setup shown in schematic form in cross section for inactivation of *E. coli* bacteria in an agar biofilm, FIG. 3. an alternative experimental setup shown in schematic form in cross section for inactivation of *E. coli* bacteria in an agar biofilm, FIG. 4. an experimental setup shown in schematic form in cross section for inactivation of *S. gordonii* bacteria initially adhered directly to a BDD anode.

Figure 5:
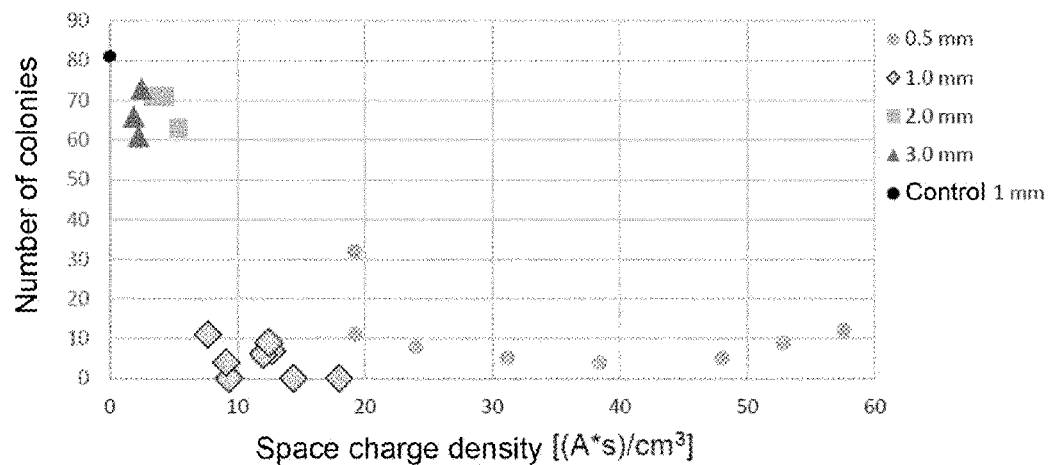
Figure 6:
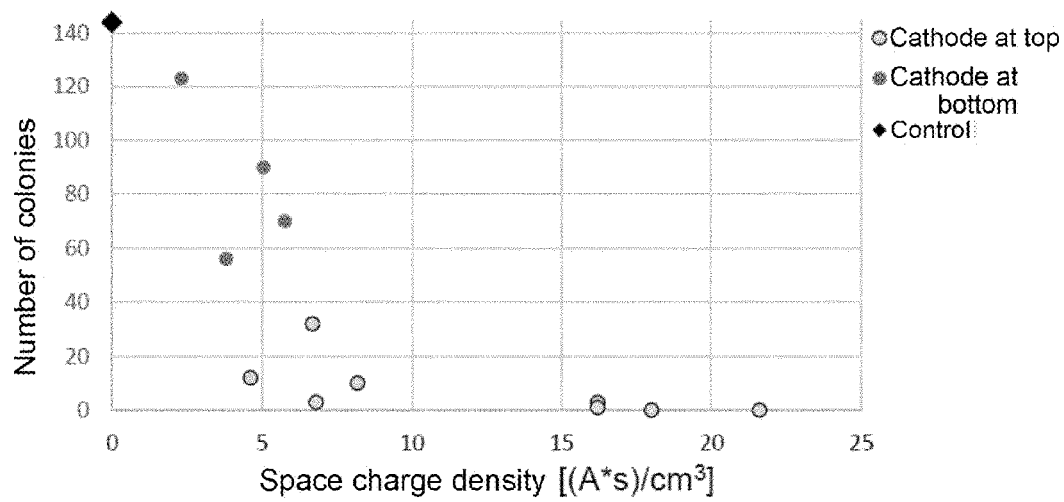
Figure 7:
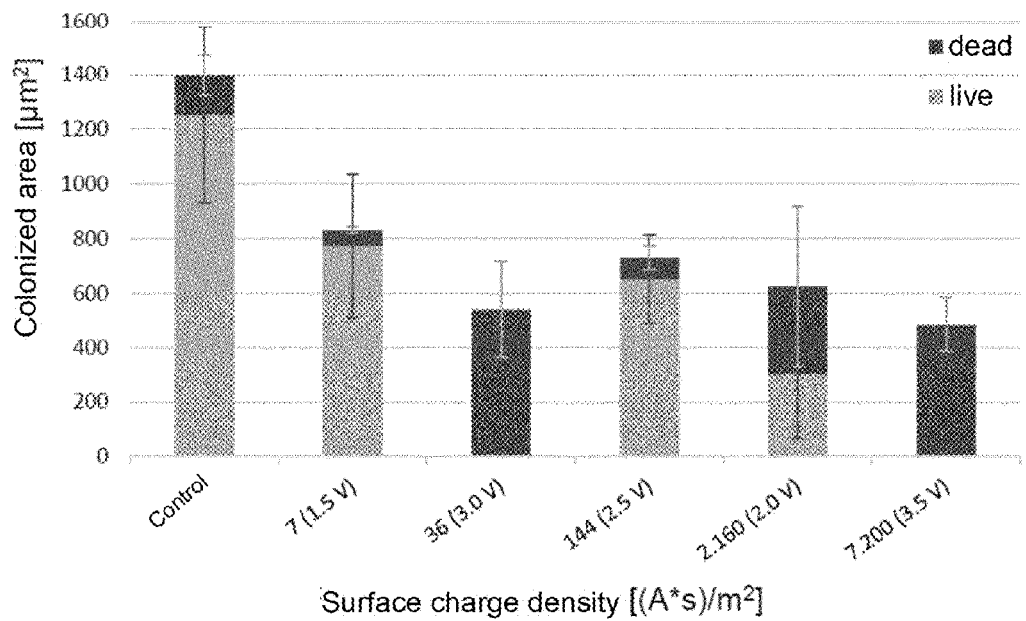
Figure 8:
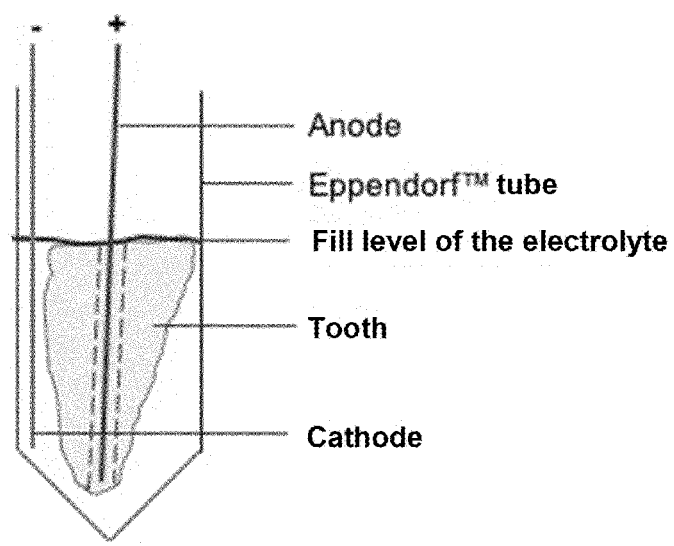
Figure 9:
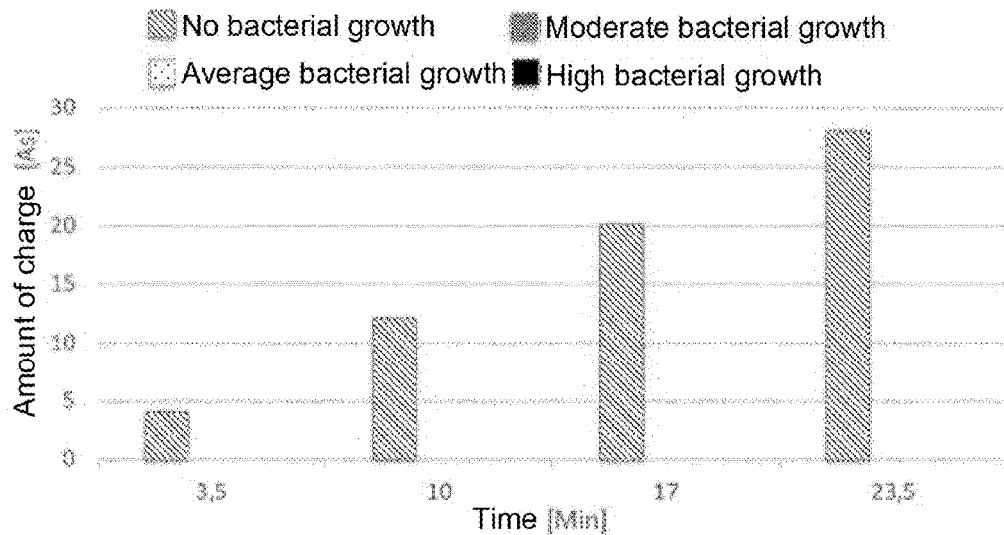
Figure 10:
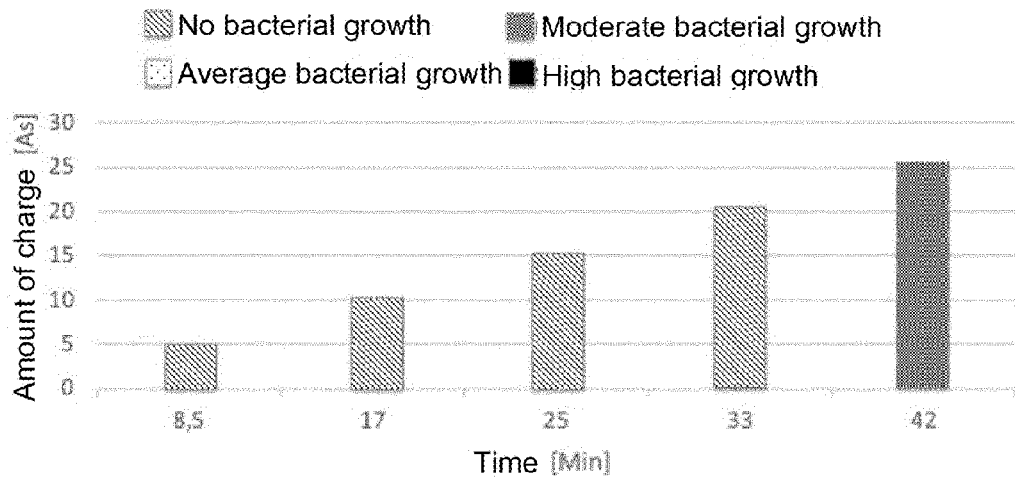

FIG. 5 a diagram to show the dependence of the number of *E. coli* colonies on space charge density at a constant voltage of 4.2 V, FIG. 6 a diagram to show the number of *E. coli* colonies as a function of space charge density and experimental setup, FIG. 7 a diagram to show the area colonized by *S. gordonii* on BDD-coated titanium platelets as a function of surface charge density and voltage applied, FIG. 8 an experimental setup shown in schematic form in cross section for inactivation of *Staphylococcus epidermidis* and *Bacillus subtilis* in a drilled root canal of a human tooth, FIG. 9 a diagram to show the dependence of the growth of *Staphylococcus epidermidis* on the amount of charge and the duration of treatment of the root canal and FIG. 10 a diagram to show the dependence of the growth of *Bacillus subtilis* on the amount of charge and the duration of treatment of the root canal.

EXPERIMENTAL

CVD Diamond Coating of Titanium Platelets

The substrate material used was pure titanium according to ASTM Standard F-67 Grade 4 and according to ISO Standard 5832-2 from L. Klein S A. The chemical composition is shown in table 2 below.

TABLE 2

Chemical composition of Grade 4 titanium according to ASTM Standard F-67.

| C | N | O | Fe | H | Ti |
|---|---|---|---|---|---|
| 0.0050% | 0.0035% | 0.2650 | 0.0200% | 0.0032% | balance |

The sample wafers separated therefrom by means of an Accutom (from Struers) have a diameter of 12 mm and a height of 1.8 mm.

A standard sample pretreatment was conducted, consisting of the steps of fine blasting, etching and seeding. The fine blasting was effected manually with silicon carbide (SiC) particles on a system from Wassermann. To establish different roughnesses, finer F320 (17 to 74 μm) SiC particles were used for a smoother titanium surface or coarser F80 (125 to 300 μm) SiC particles for a rougher titanium surface. The jet pressure was about 2.5 bar. This was followed by etching between 80° C. and 90° C. in aqueous solution of 10% $H_2SO_4$ and 10% HCl for 10 min. This increases the micro-roughness of the substrate surface. In the last step, the samples were seeded with a dilution of the 5% by weight aqueous nanodiamond particle solution from Carbodeon in an ultrasound bath for 5 min. This increases the seed density on the substrate surface as a prerequisite for a continuous diamond layer. For this purpose, the "ANDANTE" diamond suspension from Carbodeon Ltd. Oy, Pakkalankuja 5, 01510 Vantaa, Finland was used in a ratio of 1:1000 with ethanol.

The coating and filament insertion processes were conducted with the CemeCon Hot Filament CVD (HFCVD) CC800 Dia-8 system. The copper filament holders were disposed in rails 1 and 2 in both processes and were each strung with 42 tungsten wires having a length of 220 mm. The filament material used was AKS-doped tungsten wire with diameter 0.11 mm.

The insertion processes took place at a starting pressure of 6500 mPa, process pressure 6 mbar, a methane flow of 16 min and hydrogen flow 1000 min over a period of 18 h. A two-channel pyrometer placed in front of the viewing window of the closed HFCVD system was used to monitor the filament temperature. 50 titanium platelets were coated with microdiamond and 30 titanium platelets with nanodiamond. In all HFCVD processes, the starting pressure was 6000 mPa and the process pressure 6 mbar. The sample temperature of 820° C. and the filament temperature of 2160° C. were established by closed-loop control. Each coating process consists of three segments with different gas flows. The difference between micro- and nano-coating processes lies in the methane content, which is higher in the case of nano-coating. Table 3 below shows the process parameters of the diamond coatings.

TABLE 3

Process parameters and properties of the micro- and nanodiamond coatings.

| Process number | Process duration [h] | H$_2$ flow [mln] | CH$_4$ content [%] | TMB content [mln] | Current [A] | Layer thickness [μm] |
|---|---|---|---|---|---|---|
| K518 | 1.5/ | 3000/ | 1.6 | 0.27/ | 80/ | 2.5 (F80)/ |
| Mikro | 10.5/ | 2000/ |  | 0.18/ | 82/ | 1.5 |
| F80/F320 | 0.02/ | 1000 |  | 0.00 | 15 | (F320) |
| K561 | 1.5/ | 3000/ | 1.6 | 0.27/ | 60/ | 8.2 |
| Mikro | 12.5/ | 2000/ |  | 0.18/ | 86/ |  |
| F320 | 0.02 | 1000 |  | 0.00 | 15 |  |
| K571 | 1.5/ | 3000/ | 1.6 | 0.27/ | 60/ | 6.1 |
| Mikro | 18.5/ | 2000/ |  | 0.18/ | 80/ |  |
| F320 | 0.02 | 1000 |  | 0.00 | 15 |  |
| K553 | 1.5/ | 3000/ | 3.0/ | 0.27/ | 80/ | 0.8 |
| Nano | 12.5/ | 2000/ | 3.5/ | 0.18/ | 84/ |  |
| F320 | 0.02 | 1000 | 1.6 | 0.00 | 15 |  |
| K575 | 1.5/ | 3000/ | 3.0/ | 0.27/ | 80/ | 3.7 |
| Nano | 18.5/ | 2000/ | 3.5/ | 0.18/ | 88/ |  |
| F320 | 0.02 | 1000 | 1.6 | 0.00 | 15 |  |

Inactivation of *Escherichia coli*

Production of an *E. coli* Agar Biofilm

Synthetic biofilms were produced by adding nonpathogenic *Escherichia coli*-K12 498 (*E. coli*) from the German Collection of Microorganisms and Cell Cultures GmbH (DSMZ) from a preculture in liquid standard 1 growth medium (St. 1). St. 1 with agar-agar is referred to hereinafter as St. 1 agar. The constituents of this St. 1 agar are listed in table 4 below.

TABLE 4

Ingredients of the standard 1 agar growth medium in 400 ml of demineralized water.

| Ingredients | Amount [g] | Manufacturer/article number |
|---|---|---|
| Glucose monohydrate | 0.44 | Carl Roth GmbH/6780.1 |
| Sodium chloride | 2.34 | Carl Roth GmbH/3957.1 |
| Agar-agar | 8.00 | Carl Roth GmbH/5210.3 |
| Yeast extract | 1.20 | Carl Roth GmbH/2363.3 |
| Peptone from casein | 6.00 | Merck KGaA/1.02239.0500 |

The pH was adjusted to 7.4 by means of addition of sodium hydroxide. Plated out in petri dishes, the St. 1 agar solidified after a few minutes and served as culture medium. 10 ml of St. 1 agar was introduced into a centrifuge tube and kept in liquid form in a water bath at 50° C.

1000 *E. coli* bacteria were introduced into the 10 ml of liquid (50° C.) St. 1 agar and, after homogenizing, pipetted into autoclaved plastic rings of different height according to table 5 below.

TABLE 5

Amount of St. 1 agar with *E. coli* per plastic ring.

| Ring height [mm] | Amount of St. 1 agar with *E. coli* [μl] |
|---|---|
| 0.5 | 50 |
| 1.0 | 90 |
| 2.0 | 150 |
| 3.0 | 200 |

Test Setup for Inactivation of *E. coli* in Agar Biofilm

The resulting biofilm having a diameter of 8 mm was between a microdiamond-coated anode 12 of titanium and a stainless steel sheet as cathode 16 during the experiment. A titanium rod 10 was used for contacting of the anode 12 and cathode 16 in that it was pressed manually on to the coated anode 12 or the cathode 16. In the experimental setup shown in FIG. 2, the titanium rod 10 is connected to the plus pole and the stainless steel sheet to the minus pole of a power source. Beneath a sterile safety cabinet, voltages of 4.0 V, 4.2 V and 4.5 V were applied for between 1 min and 6 min and the respective corresponding current flow was measured.

In order to rule out diffusion of the hydrogen gas formed at the cathode from below through the biofilm in the upward direction and hence inactivation of *E. coli* by hydrogen, anode 12 and cathode 16 were exchanged in some experiments. The corresponding experimental setup is shown in FIG. 3.

Quantification of the Bacterial Colonies

Subsequently, the treated biofilms were separated from the rings and they were positioned on solid St. 1 agar culture media in petri dishes. They were incubated at 27° C. for about 7 days.

The colonies formed within the biofilms were apparent as dark spots by the naked eye and were counted under 40-fold magnification under a light microscope.

Inactivation of *Streptococcus gordonii*

Initial Adhesion of *Streptococcus gordonii*

The BDD-coated titanium platelets were initially bacterially colonized. The culture medium used in a preculture was autoclaved Tryptone Soya Broth (TSB) to which yeast extract had been additionally added. The constituents of the culture medium are listed in table 6 below.

TABLE 6

Ingredients of the Tryptone Soya Broth culture medium with yeast extract in 1 l of tridistilled water.

| Trade name | Amount | Manufacturer/Art. No. |
|---|---|---|
| Tryptone Soya Broth | 30.0 g | Oxoid LTD |
| Yeast extract | 3.0 g | Carl Roth GmbH/2363.3 |

50 ml of the culture medium was inoculated with 50 μl of the oral bacterium *S. gordonii* DSMZ 20568 in an Erlenmeyer flask and aerobically incubated at 37° C. while stirring for 18 h. Subsequently, the resulting culture was transferred to a 50 ml centrifuge tube and centrifuged at 4° C. for 15 min and 4000 g. The supernatant was poured off and the pellet was resuspended in 50 ml of a 50 mM tris(hydroxymethyl)aminomethane solution that had been adjusted to pH 7.5 by means of hydrochloric acid (HCl) (TRIS HCl). Subsequently, 25 ml of TRIS HCl was made up to 500 ml with tridistilled water. The steps of centrifuging and resuspending were repeated twice more. In the last resuspension, only 20 ml of the 50 mM TRIS buffer was used, and this was followed by vortexing for 5 min. By means of the buffer solution used, the resulting bacterial suspension was adjusted to an optical density (OD) of 0.7 at a wavelength of 600 nm. Each of the coated titanium platelets was placed with its coating upward into one of the wells of a 6-well plate from Greiner Bio-One. 3 ml of the bacterial suspension was placed onto each of the coated titanium platelets.

Initial adhesion took place at 37° C. in an incubator at ventilation level 3 with slight rotation at 150 revolutions per minute within 5 h. The colonized platelets were washed twice with 3 ml each time of Dulbecco's phosphate-buffered saline (PBS). Each well was filled to the brim with PBS for the experiment.

Experimental Setup for Inactivation of Initially Adhered *Streptococcus Gordonii*

The experimental setup is shown in FIG. 4. At the base of each of the PBS-filled wells 22 were the BDD-coated and bacterially colonized titanium platelets that were connected as anode 12 in the electrochemical experiment. A titanium-aluminum rod 18 of diameter 2 mm made contact with the anode 12. The cathode 16 made of stainless steel with diameter 22 mm was in a round recess in the PVC lid 20 that was fitted to the diameter of the well 22 of 40 mm. The titanium-aluminum rod 18 was guided through a hole in the cathode 16 to make contact with the anode 12. Teflon served as insulation material between the two electrodes. The titanium-aluminum rod 18 was connected to the plus pole, while the cathode 16 was attached to the minus pole of a power source. A series-connected multimeter detected the current flow with voltage applied. Applying the voltage gave rise to an electrical field 24 between the anode 12 and the cathode 16.

The stimulation was followed by a washing operation with 3 ml of PBS in order to remove the detached bacteria. The live/dead distribution on the platelets was determined using a live/dead stain of the adhered streptococci with fluorescent dyes. For this purpose, the green live dye SYTO9 and the red dead dye propidium iodide from the Live/Dead BacLight Bacterial Viability Kit from Thermofisher Scientific were used. 3 ml of a staining solution in which each of the two dyes was diluted 1:1000 with PBS wetted all the platelets. Since both dyes are light-sensitive, the staining process took place under darkened conditions. The contact time was about 30 min. The live dye binds to the DNA of all bacterial cells, while the dead dye penetrates solely into bacteria with a destroyed membrane and displaces the live dye. Thereafter, the staining solution was replaced by the same amount of 2.5% glutaraldehyde as fixative. This is a highly reactive acidic solution that crosslinks proteins in the bacterial membrane by reaction with amino groups and hence kills the bacterial cells. Before the microscope characterization, after a contact time of at least 15 min, the fixing solution was exchanged for PBS.

In the first experiments, voltages between 1.5 V and 3.5 V were applied for 2 min or 3 min. These results were used to calculate the charge density needed to kill the adhered bacteria, and this was established in a controlled manner in subsequent experiments. The surface charge densities here were from 18 (A*s)/m² to 18 000 (A*s)/m².

Every experiment in which charge densities were set was conducted three times in independent biological replicates. Comparisons took place between micro- and nanodiamond coating, and between diamond coating and straight titanium platelets.

Inactivation of Human Gingival Fibroblasts

In order to test the influence of the bacterial inactivation by means of free-radical formation on BDD-coated implant surfaces on the surrounding tissue, an experiment with six BDD-coated titanium platelets was used, one of which served as untreated control.

The tissue cells used were human gingival fibroblasts from the gum. These primary cells have been isolated from tissue that was still intact immediately beforehand. The preculture grew within three days in DMEM cell culture medium (from Merck Millipore) with the ingredients apparent from table 7 below, 10% fetal calf serum and 1% penicillin.

TABLE 7

Ingredients of the DMEM cell culture growth medium in 0.5 l of tridistilled water.

| Trade name | Amount |
| --- | --- |
| Sodium hydrogencarbonate | 3.7 g/l |
| D-Glucose | 4.5 g/l |
| L-Glutamine | 0.6 g/l |

50 000 cells in 120 µl of a cell suspension were sown on each of the BDD-coated titanium platelets. The cells here were in the eighth passage. The platelets were incubated at 37° C. and 5% $CO_2$ for 2 h. The pH of the cell culture medium here was about 7.7. After the adhesion of the fibroblasts, each of the six platelets in the wells 22 were wetted with 3 ml of DMEM cell culture medium and incubated for 24 h. This was followed by treatment in PBS with the experimental setup shown in FIG. 4 and the same charge densities as in the case of initial adhesion and biofilm from *S. gordonii*. Thereafter, replacement of the PBS with 3 ml per well of the staining solution took place. Each of the two dyes has been diluted 1:1000 therein with PBS. The live dye used was calcein from Invitrogen, the dead dye propidium iodide from SIGMA. The experiment was evaluated using five photographs per platelet with the Zeiss Axio Scope Al microscope in 200-fold magnification.

Results and Discussion

All results are plotted against electrical charge density as a measure of the bactericidal oxidizing agents formed. This was either specifically established in the experiment or calculated subsequently. For this purpose, it was necessary to know the current measured at the voltage applied, the corresponding treatment time and the volume of the biofilm or the area of adhered bacteria.

The charge distribution in a volume is referred to as space charge density e.

$$[\varrho] = 1 \frac{As}{m^3}$$

The uniform distribution of the charge over any area is referred to as surface charge density σ.

$$[\sigma] = 1 \frac{As}{m^2}$$

Inactivation of *Escherichia coli* in an Agar Biofilm

*E. coli* Inactivation in Different Biofilm Volumes

The diagram in FIG. 5 illustrates an experiment in which each biofilm was subjected to a load of 4.2 V for 2 min with the cathode 16 positioned at the top according to the experimental setup shown in FIG. 3. Each point on the graph is the averaged number of colonies from three sites in a biofilm. It is clearly apparent that, with this constant voltage and treatment time, higher space charge densities occur in thinner biofilms than in the thicker biofilms and hence more colonies are inactivated there. Within identical biofilm heights, owing to different contact resistances and associated varying current intensities, different space charge densities arise. In the biofilms of height 2 mm and 3 mm, there is barely any difference in the space charge densities and the number of colonies, while the thinner biofilms include far fewer colonies. Complete elimination takes place from about 10 (A*s)/cm$^3$. The volume of the 0.5 mm biofilms corresponds to 0.025 cm$^3$, the volume of the 1 mm biofilms to 0.05 cm$^3$, the volume of the 2 mm biofilms to 0.1 cm$^3$, and the volume of the 3 mm biofilms to 0.16 cm$^3$.

FIG. 5 shows the dependence of the number of E. coli colonies on space charge density at a constant voltage of 4.2 V for various biofilm volumes. Overall, the number of bacterial colonies drops with increasing space charge density. In the thinner biofilms, the bacteria are more intensely inactivated since higher space charge densities are attained therein.

Comparison of Two Different Arrangements of the Cathode

In order to check whether the evolution of hydrogen at the cathode enhances bacterial inactivation by hydroxyl radicals and other oxidizing agents, the position of the cathode was varied, as illustrated in FIG. 2 and FIG. 3.

It was expected that atomic hydrogen with the cathode at the bottom would diffuse up through the biofilm and possibly be able to kill bacteria. However, the results in this case show lower inactivation of E. coli as a result of inadequate space charge densities. If the construction is reversed and the cathode positioned at the top, contact resistances are lower, and hence the space charge densities are higher and more bacteria die. This is shown in FIG. 6 in the case of an experiment with 4.2 V and 1 mm-thick agar biofilms.

FIG. 6 shows the number of E. coli colonies as a function of space charge density. This involved comparing the experimental setup according to FIG. 2 and FIG. 3 for inactivation of E. coli at 4.2 V in 1 mm-thick agar biofilms for 1 and 3 min. It was found that, with the cathode disposed at the bottom, no increased bacterial inactivation by the hydrogen formed took place.

Summary of Inactivation of Escherichia coli in an Agar Biofilm

In general, in all experiments with different biofilm volumes, it was found that more bacterial colonies were inactivated by higher space charge densities, and space charge density, by definition, was inversely proportional to biofilm height.

It was found that E. coli can be completely inactivated by electrochemical treatment with diamond anodes. At 4.0 V and 4.2 V, the minimum charge density needed for the purpose in 1 mm-thick biofilms is 2 (A*s)/cm$^3$ and 10 (A*s)/cm$^3$ respectively for 2 min.

It was not possible to demonstrate inactivation of E. coli by hydrogen formed at the cathode in the experimental setup according to FIG. 2.

Elimination of E. coli by evolution of high temperature during the electrochemical experiment was likewise examined and was ruled out.

Inactivation of Initially Adhered Streptococcus gordonii

The results that follow relate to electrochemical experiments in a liquid electrolyte. The experimental setup is shown in FIG. 4.

Owing to a very small height of the individually adhered S. gordonii and of the biofilms, which is less than 30 µm, the live/dead distribution in the diagrams here was based on the surface charge density.

Determining of the Voltage for Bacterial Inactivation

The voltage range in which an oxidizing agent-implemented disinfection of the BDD-coated surface of the titanium platelets colonized by bacterial adhesion with S. gordonii was to be observed was determined.

FIG. 7 shows the average area per sample colonized by S. gordonii by initial adhesion to BDD-coated titanium platelets after application of various voltages as a function of the calculated surface charge density in (A*s)/m$^2$ and the voltage applied. All five samples are treated for 2 min. No voltage was applied to the colonized control. The standard deviations show the variation of the five measurement points within a sample. Only few dead cells that have died off naturally are present on the untreated control. In the case of the titanium platelets treated at 1.5 V and 2.5 V, the dead fraction is comparable to that of the control. However, the live fraction in these samples is much lower than that of the control. It is likely that fewer microbes found survival conditions for colonization or the microbes were washed off more easily in the washing operation. A very high area fraction of dead bacteria is shown by the samples to which 3.0 V and 3.5 V were applied. Virtually all oral microbes were inactivated at these voltages.

The comparison of different voltages on boron-doped microdiamond-coated platelets (K571) indicates that the transition from live to dead S. gordonii microbes takes place between 2.5 V and 3.0 V.

Experiments with boron-doped micro- and nanodiamond coatings, which are not shown, did not show any crucial influence of the diamond structure on the electrochemical inactivation of S. gordonii. The morphology of diamond merely affects the number of adhered bacteria, but not the inactivated fraction thereof.

Influence of the Oxidizing Products on Human Gingival Fibroblasts

An experiment with human fibroblasts from the gum under the same conditions as in the experiments conducted with S. gordonii did not show any killing of the eukaryotic cells. Under treatment with the highest charge densities, exclusively green-stained live fibroblasts are apparent. It can be concluded from this that electrochemical surface disinfection is possible in principle in the oral cavity with voltages of up to 3.5 V and surface charge densities of 18 000 (A*s)/m$^2$.

Conclusion

The inventors were able to show that a boron-doped diamond coating on an anode can be used to completely electrochemically inactivate both Gram-negative Escherichia coli bacteria and Gram-positive Streptococcus gordonii species. This means that BDD-coated implants make it possible to electrochemically prevent inflammation reactions and control infections.

Electrochemical therapy of a microbial infection at a BDD-coated implant surface with comparatively low voltage and charge density is tolerated by the human or animal body without difficulty for the short treatment time required for the purpose. If required, the treatment can be repeated or stopped at any time.

Since numerous oxidizing agents are formed directly at the diamond anode in the therapy, bacteria can be inactivated directly and effectively at the implant surface. Fibroblasts did not react negatively to this treatment in an experiment.

Inactivation of Staphylococcus epidermidis and Bacillus subtilis in a Drilled Root Canal of a Human Tooth Extracted human teeth with a drilled root canal were obtained from a dentist. The teeth were first incubated for at least 20 hours in a physiological saline containing either Staphylococcus epidermidis or Bacillus subtilis. The root canals were colonized here with the respective bacteria. Subsequently, the teeth were rinsed with physiological saline and placed in physiological saline as electrolyte in the experimental setup shown in FIG. 8. The anode here consisted of a boron-doped diamond-coated niobium wire, and the cathode of steel. A voltage in the range from 5 to 9 volts was applied, such that the amounts of charge specified in the figures have flowed within the period of treatment specified in each case.

After the period of treatment specified in each case, the respective tooth was split and the resultant inner split surfaces including the surface of the root canal were impressed repeatedly on an St.1 agar culture medium and finally stored with this surface on the agar. The agar culture medium was then incubated at 27 degrees for 1-2 days. Bacterial growth was apparent from the formation of colonies. The colonies were apparent to the naked eye as dots and were subjectively categorized into no, moderate, average and high bacterial growth.

Inactivation of *Staphylococcus epidermidis*

The results apparent from FIG. 9 show that complete sterilization of the inner root canal surface was achieved even with an amount of current of 4 As, corresponding to a treatment time of 3.5 minutes. No bacterial growth was found on any of the agar culture media.

Inactivation of *Bacillus subtilis*

The results apparent from FIG. 10 show that complete sterilization of the inner root canal surface was found even with an amount of current of 5 As, corresponding to a treatment time of 8.5 minutes. Moderate bacterial growth found after a treatment time of 42 minutes and with an amount of current of 25 As may have been caused by the ability of *Bacillus subtilis* to form spores and the possible presence of these spores in the dentinal tubules of the root canal. It was additionally found that, in the event of spore formation, the amount of charge required for complete sterilization can increase by more than one hundred times.

Results and Discussion

The experiments conducted on an extracted tooth show that a boron-doped diamond-coated anode is of good suitability for disinfection of a root canal with a comparatively short time. Such an anode, for example in the form of a boron-doped diamond-coated wire, can be introduced for the purpose into an open root canal and energized in a dental treatment. The cathode required for the purpose may be placed close to the tooth to be treated within the oral cavity. The coated wire to be introduced into the root canal is an implant for the purposes of the invention.

In a dental treatment, it is also conceivable that a tool used for dental treatment, for example a drill, is coated with boron-doped diamond and is connected as anode in the treatment. Such a tool is then a surgical tool for the purposes of the invention.

LIST OF REFERENCE NUMERALS

10 titanium rod
12 anode
16 cathode
18 titanium-aluminum rod
20 lid
22 well
24 electrical field

The invention claimed is:

1. A therapeutic method, comprising treating microbial infection caused by bacteria on an implant in a human or animal body with oxidizing products having antimicrobial action that have been produced on an implant made of a metal or having a surface made of a metal, wherein the implant has, on its/the surface, a coating with polycrystalline doped electrically conductive diamond, wherein the therapeutic treatment comprises the generation of the products having antimicrobial action directly on the implant, wherein the products having antimicrobial action are $C_2O_6^{2-}$, $S_2O_8^{2-}$ and/or $P_2O_8^{4-}$ ions,
   wherein the implant is connected as anode in an electrochemical system in the body, wherein the electrochemical system comprises, in addition to the anode, a cathode, a power source connected in an electrically conductive manner to the anode and to the cathode, and an electrolyte comprising or consisting of a body fluid, or consists of the anode, a cathode, a power source connected in an electrically conductive manner to the anode and to the cathode, and an electrolyte comprising or consisting of a body fluid, or
   wherein the implant is disposed within an electrical field, by means of which a negative charge is induced at a first site and a positive charge at a second site by induction on the implant, by means of which the first site becomes the anode in an electrochemical system and the second site becomes the cathode in the electrochemical system, wherein the electrochemical system comprises, in addition to the implant, an electrolyte comprising or consisting of a body fluid or consists of the implant and an electrolyte comprising or consisting of a body fluid, wherein an anodic electrode potential in the range of 1.80 V to 2.07 V is applied to the electrochemical system in order to generate the $C_2O_8^{2-}$, $S_2O_8^{2-}$ and/or $P_2O_8^{4-}$ ions directly on the implant.

2. The method of claim 1, wherein the diamond has been doped with boron or phosphorus.

3. The method of claim 1, wherein the microbial infection is a bacterial infection or a fungal infection.

4. The method of claim 1, wherein the metal is titanium or a titanium-containing alloy.

5. The method of claim 4, wherein the alloy is Ti-6Al-4V, Ti-6Al-7Nb or another alloy containing, in addition to titanium, aluminum and/or niobium and/or iron and/or molybdenum.

6. The method of claim 1, wherein the coating is a coating produced on the surface of the implant in a gas phase containing a boron containing compound by hot filament chemical vapor deposition (HFCVD) or by microwave plasma-assisted chemical vapor deposition (MPCVD) or by another kind of chemical vapor deposition (CVD).

7. The method of claim 1, wherein the metal is titanium or the titanium-containing alloy and there is an interlayer of titanium carbide between the titanium or the alloy and the coating.

8. The method of claim 7, wherein the interlayer has a layer thickness of not more than 3 μm.

9. The method of claim 7, wherein the interlayer has a layer thickness of at least 100 nm.

10. The method of claim 8, wherein the interlayer has a layer thickness of at least 100 nm.

11. The method of claim 1, wherein the implant is a dental implant or jaw implant which is accessible from outside the body without surgical intervention and is electrically contacted for the therapy from outside the body, or wherein the implant has been implanted within the body and an electrical conductor, especially an electrically conductive wire, is routed from the implant to an outside of the body and is electrically contacted on the outside for the therapy or is routed from the implant to a contact site beneath the skin that is electrically contacted for the therapy from the outside through a puncture or is routed from the implant via an electrical rectifier to a coil, especially disposed not more than 3 cm beneath the skin, and is connected thereto in an electrically conductive manner, wherein the coil additionally has electrically conductive connection via the electrical rectifier to the cathode, wherein the cathode is likewise disposed within the body, wherein, for the therapy, a flow of current is induced in the coil by induction from outside the body, by means of which the cathode and the anode are energized.

12. The method of claim 1, wherein the electrical field is built up between at least two plates of a capacitor or by means of at least one electrical coil or is built up between a further anode and a further cathode within the electrochemical system, wherein the electrochemical system additionally comprises, in addition to the further anode and the further cathode, a power source connected in an electrically conductive manner to the further anode and the further cathode or additionally consists of the further anode and the further cathode and a power source connected in an electrically conductive manner to the further anode and the further cathode.

13. The method of claim 12, wherein the electrolyte in the electrochemical system comprises an electrically conductive auxiliary fluid or consists of the body fluid and the electrically conductive auxiliary fluid, wherein the electrically conductive auxiliary fluid in each case is a liquid that establishes electrical contact of the further anode and the further cathode with the body fluid.

14. The method of claim 1, wherein the implant is disposed within a closed region of the body, wherein a voltage applied to the electrochemical system is chosen such that the amount of gaseous further products formed at the anode is sufficiently low that these dissolve directly in the body fluid after they have formed.

15. The method of claim 1, wherein the microbial infection is a microbial infection associated with an inflammation reaction.

16. The method of claim 1, wherein the implant is an endoprosthesis made of a metal.

17. The method of claim 1, wherein the diamond is microdiamond.

18. The method of claim 17, wherein the microdiamond has a grain size ranging from 2 to 3 μm.

* * * * *